United States Patent [19]

Hon

[11] 4,321,931
[45] Mar. 30, 1982

[54] ELECTRODE STRUCTURE AND APPLICATOR THEREFOR

[76] Inventor: Edward D. Hon, 11 Bradbury Hills Rd., Bradbury, Calif. 91010

[21] Appl. No.: 21,550

[22] Filed: Mar. 20, 1979

Related U.S. Application Data

[63] Continuation-in-part of Ser. No. 895,110, Apr. 10, 1978, abandoned.

[51] Int. Cl.³ .............................................. A61B 5/04
[52] U.S. Cl. .................................................. 128/642
[58] Field of Search .............. 128/642, 785, 802, 784, 128/786, 639, 419 P

[56] References Cited

U.S. PATENT DOCUMENTS

| | | | |
|---|---|---|---|
| Re. 28,990 | 10/1976 | Hon et al. | 128/642 |
| 3,087,486 | 4/1963 | Kilpatrick | 128/642 |
| 3,750,650 | 8/1973 | Ruttgers | 128/642 |
| 3,844,292 | 10/1974 | Bolduc | 128/785 |
| 3,986,497 | 10/1976 | Dali | 128/642 |
| 4,103,690 | 8/1978 | Harris | 128/785 |
| 4,149,528 | 4/1979 | Murphy | 128/642 |
| 4,180,080 | 12/1979 | Murphy | 128/642 |

FOREIGN PATENT DOCUMENTS

| | | | |
|---|---|---|---|
| 2738479 | 3/1979 | Fed. Rep. of Germany | 128/642 |
| 1457426 | 12/1976 | United Kingdom | 128/642 |

OTHER PUBLICATIONS

Hon et al., "Electronic . . . Fetal Heart Rate", Ob. & Gyn., vol. 40, No. 3, Sep. '72, pp. 362-365.

Primary Examiner—Lee S. Cohen
Attorney, Agent, or Firm—Lewis Anten

[57] ABSTRACT

A fetal electrode applicator for attaching a coil electrode to the skin of a fetus by moving the coil electrode forwardly through the forward end of an inserter tube introduced through the mother's vagina by a plunger having cooperating helical threads for converting linear force applied to the plunger to rotary motion of the coil electrode. In one embodiment, the helical threads include cooperating helical ribs and grooves on the electrode carrier and the forward interior wall of the inserter tube, and a plunger rod pushes the electrode carrier forwardly. In the preferred embodiment, helical grooves are formed on a motion converter which carries the electrode carrier, and radially-inwardly projecting pins on the forward interior wall of a plunger tube engage the helical grooves; and stops are provided for limiting forward movement of the motion converter, whereby depression of the plunger after the coil electrode has moved forwardly a predetermined distance will result in only rotary motion of the coil electrode.

50 Claims, 21 Drawing Figures

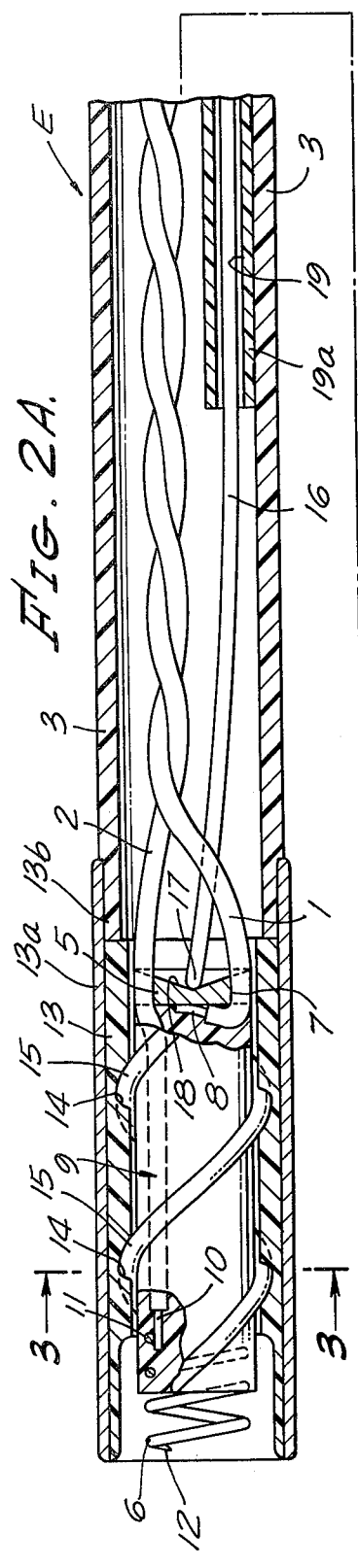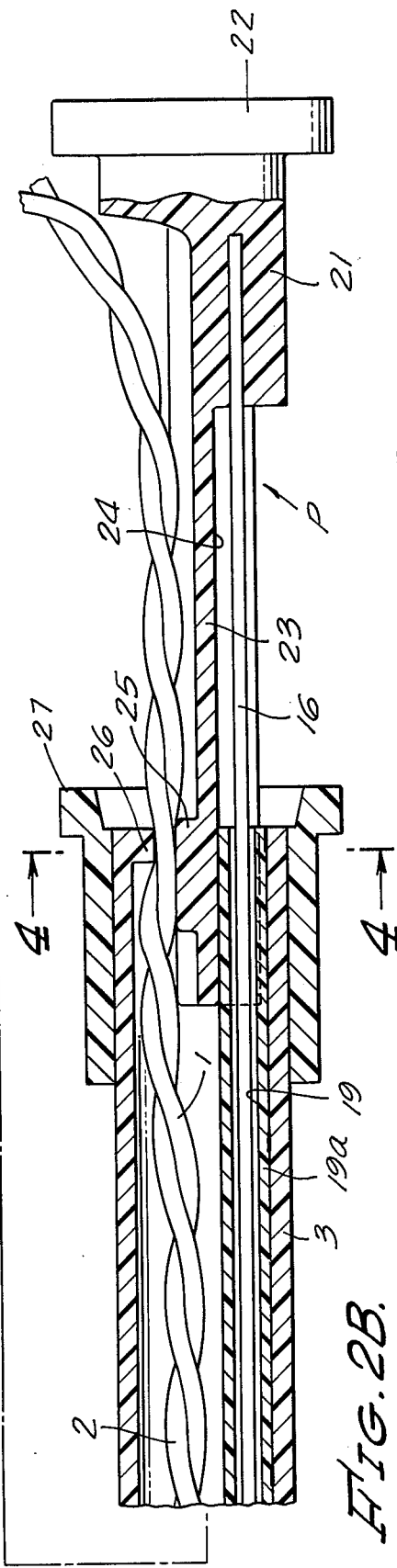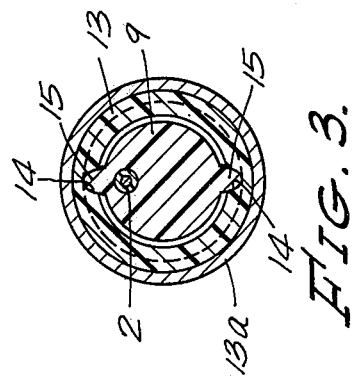

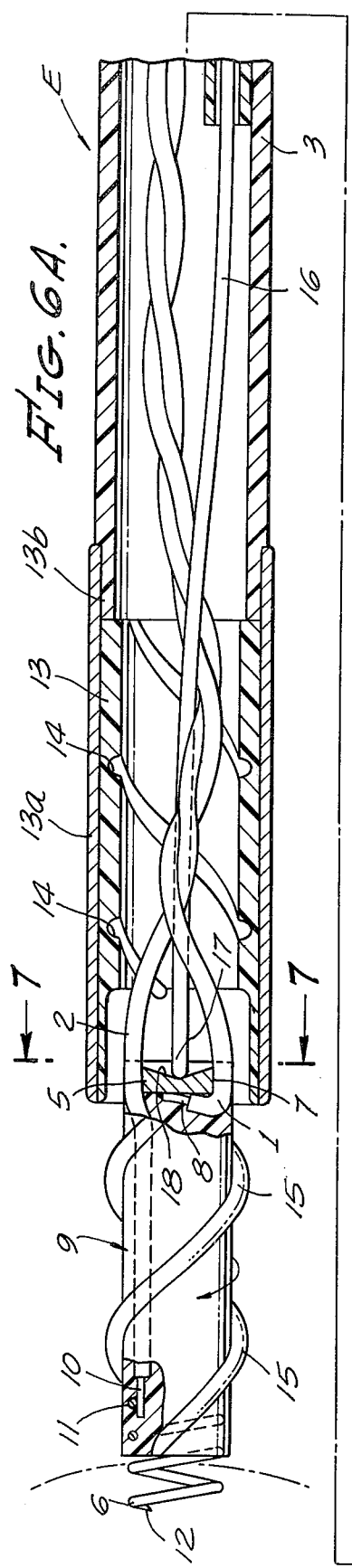
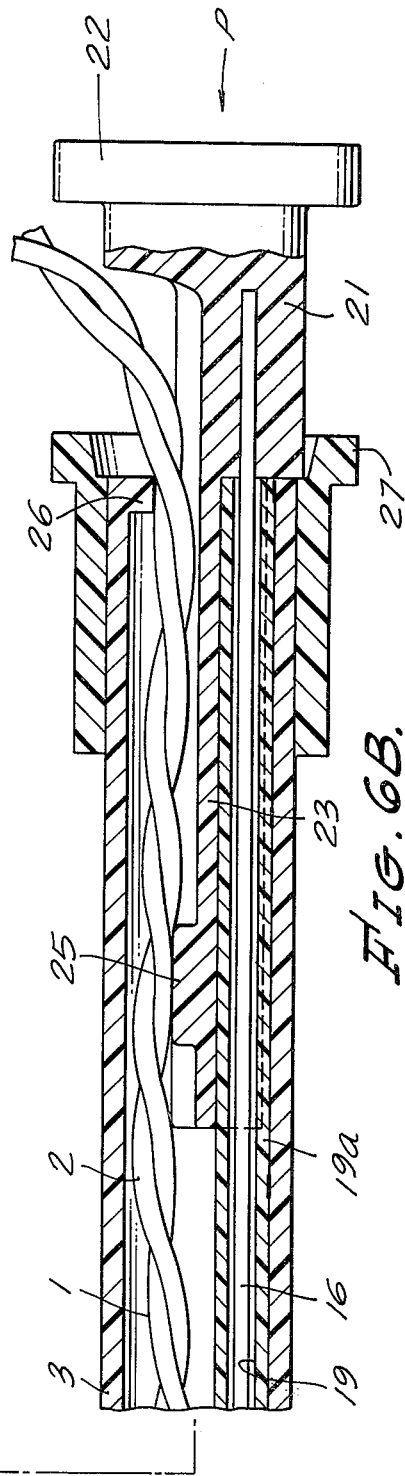
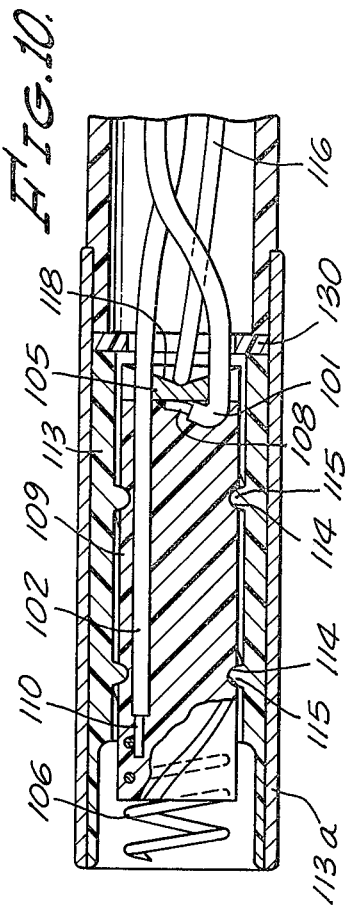
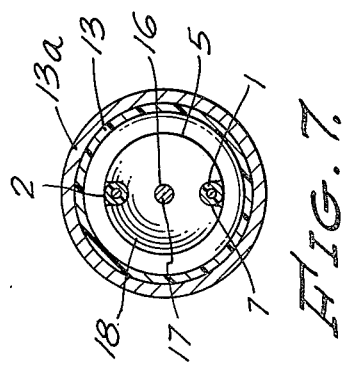

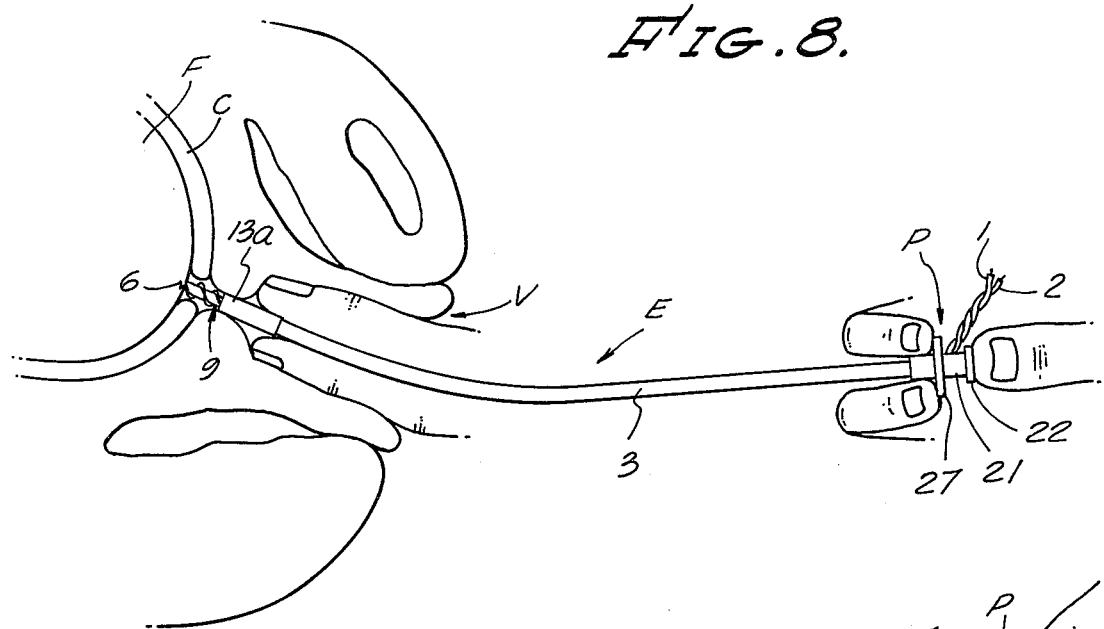
FIG.8.
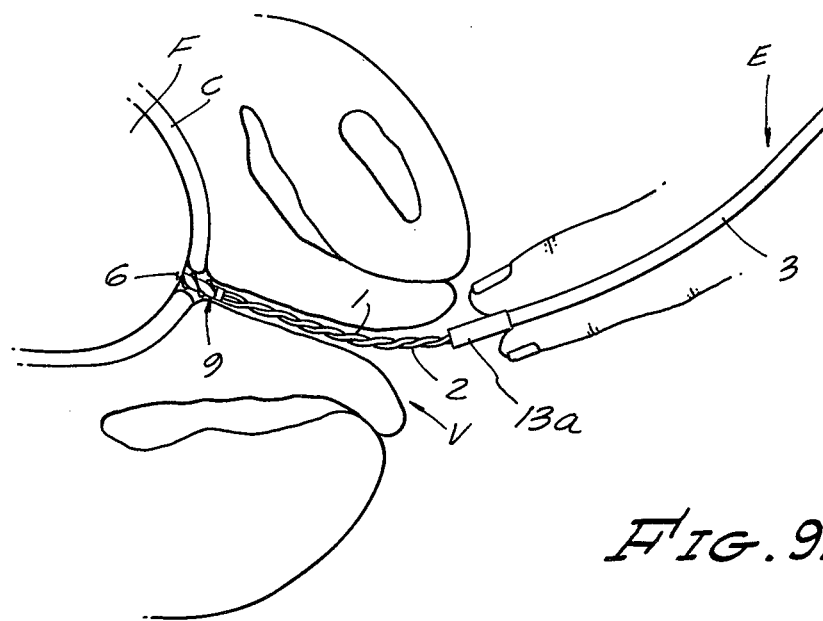
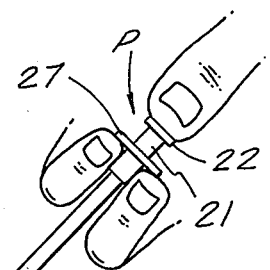
FIG.9.

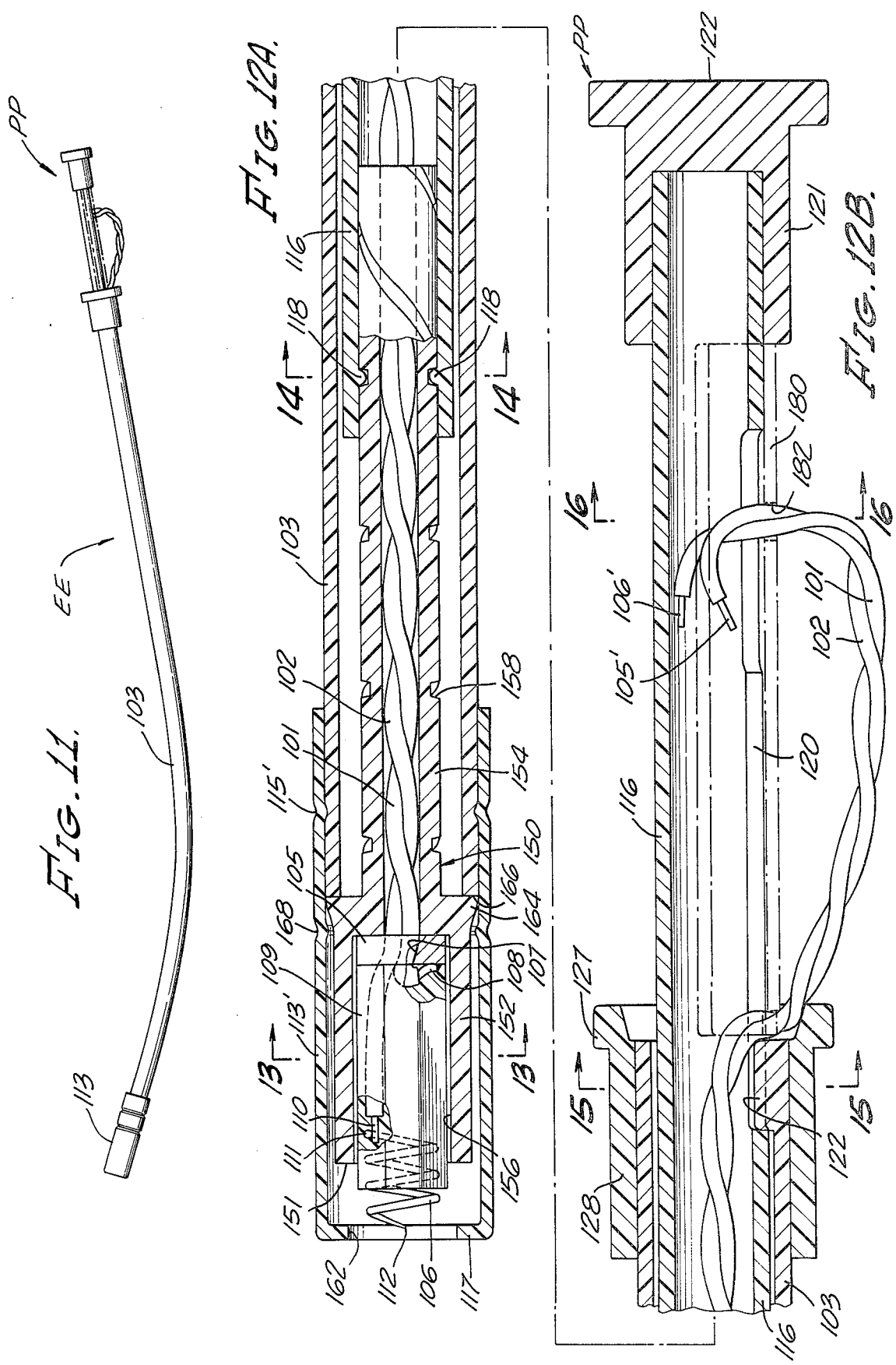

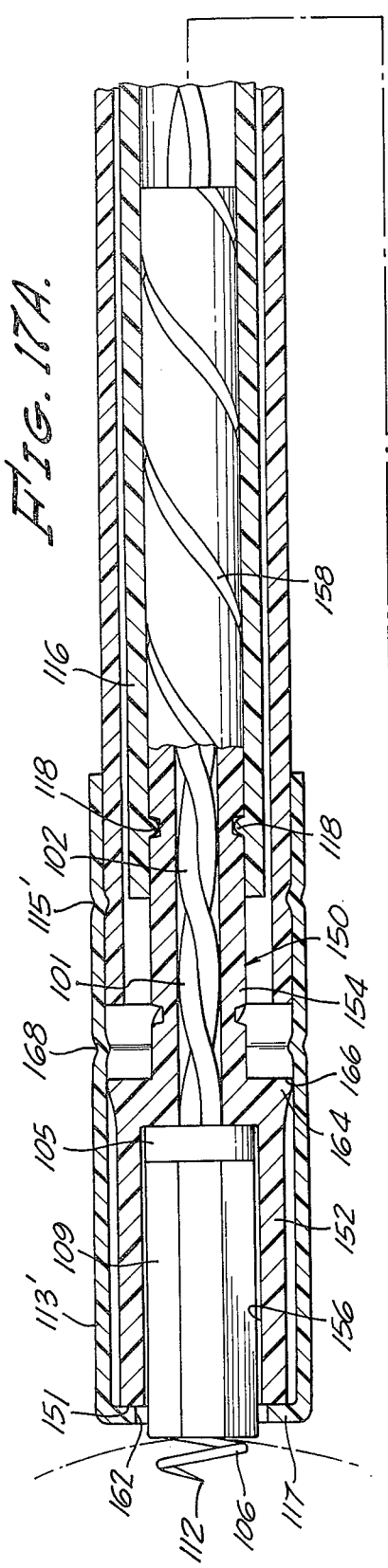
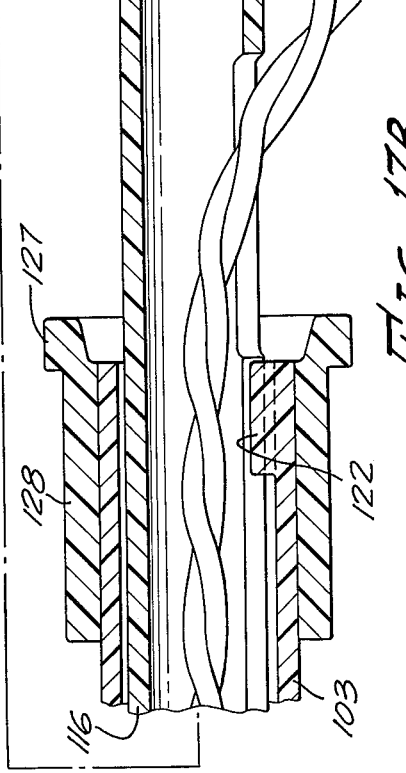
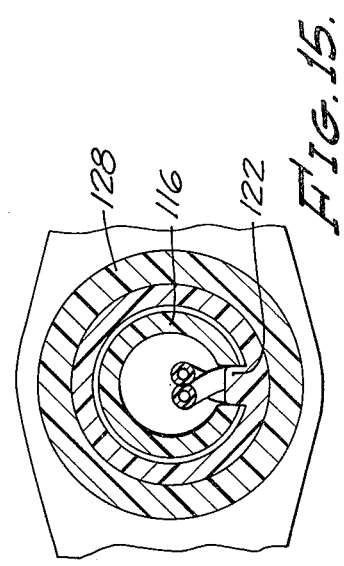
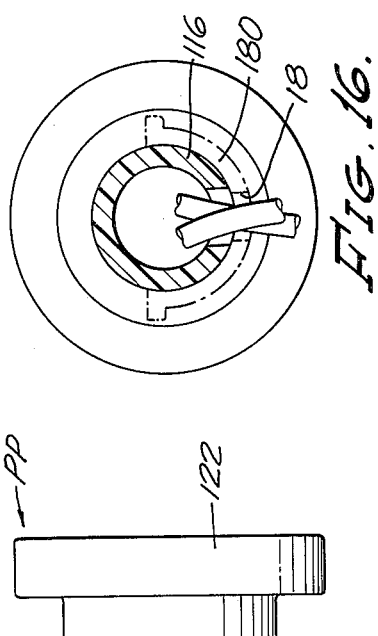

ELECTRODE STRUCTURE AND APPLICATOR THEREFOR

RELATED APPLICATION

This application is a continuation-in-part application; the parent application is U.S. patent application Ser. No. 895,110 filed Apr. 10, 1978 entitled "Electrode Structure and Applicator Therefor now abandoned."

BACKGROUND

The present invention relates to an electrode structure and applicator for inserting a bipolar electrode structure through the vagina and cervix of a woman in labor and attaching it to the epidermis of a fetus. The electrode structure is designed to be operatively connected to an amplifier and a cardiotachometer for recording the fetal electrocardiogram and heart rate during labor and delivery.

For over seventy years monitoring of fetal heart rate has been one of the important procedures in the management of labor. Recently, a number of electronic techniques have been developed for continuous recording of this data. Currently, the most successful techniques for fetal heart rate monitoring employ electrodes attached directly to the fetus.

U.S. Pat. No. Re. 28,990 is directed to an electrode structure which is believed to be the most effective type employed today in the monitoring of fetal heart rate. The state of the art prior to the development of the device disclosed in that patent is amply illustrated in the references cited during the prosecution of the application for that patent and those described in Column 1 of the patent.

The present invention represents an improvement over the invention of U.S. Pat. No. Re 28,990. The device of the present invention is, in short, safer, easier and more reliable to use. It is believed that the advantages of the present invention may be more readily appreciated following a review of the preferred embodiments described below and illustrated in the accompanying drawings. Accordingly, these advantages are discussed after the following specification, prior to the claims.

BRIEF DESCRIPTION OF THE DRAWINGS

In the drawings:

FIGS. 2A and 2B, together, constitute a sectional side elevation view of the electrode structure of the embodiment of the present invention shown in FIG. 1 with the electrode-carrying member and the plunger assembly shown in the positions they occupy prior to the time that the plunger is depressed to project the electrode carrying structure forwardly and consequently cause it to rotate.

FIG. 3 is a transverse section taken along the plane 3—3 of FIG. 2A.

FIG. 4 is a transverse section taken along the plane 4—4 of FIG. 2B.

FIGS. 6A and 6B, taken together, constitute a sectional elevation view similar to 2A and 2B but showing the improved electrode applicator structure with the electrode carrying member and plunger in the positions they occupy after the plunger has been depressed to project the electrode carrying structure forwardly and consequently caused it to rotate.

FIG. 7 is a transverse section taken on the plane 7—7 of FIG. 6A.

FIGS. 8 and 9 are diagrammatic views similar to FIG. 1, illustrating the manner in which the electrode applicator structure is actuated to attach the spiral electrode to the fetal epidermis, and the manner in which the inserter tube and plunger assembly may thereafter be removed.

FIG. 10 is a sectional side elevation view, similar to FIG. 2A, illustrating the forward end of another embodiment of the electrode applicator structure of the present invention.

FIG. 11 is a diagramatic view of a preferred embodiment of the electrode applicator structure of the present invention.

FIGS. 12A and 12B, together constitute a sectional side elevation view of a preferred embodiment of the electrode applicator structure of the present invention with the electrode carrying member and the plunger assembly shown in the positions they occupy prior to the time that the plunger is depressed to project the electrode carrying structure forwardly and rotate it.

FIGS. 13, 14, 15 and 16 are transverse sections taken along the planes 13—13, 14—14, 15—15 and 16—16, respectively, of FIGS. 12A and 12B.

FIGS. 17A and 17B, together, constitute a sectional side elevation view similar to FIGS. 12A and 12B, showing the improved electrode applicator structure of the embodiment of the present invention shown in FIGS. 11-16 with the electrode carrying member and the plunger in the positions they occupy after the applicator has been depressed to project the electrode carrying member forwardly and to rotate it.

DESCRIPTION OF THE EMBODIMENTS OF FIGS. 1-10

Figure 1:
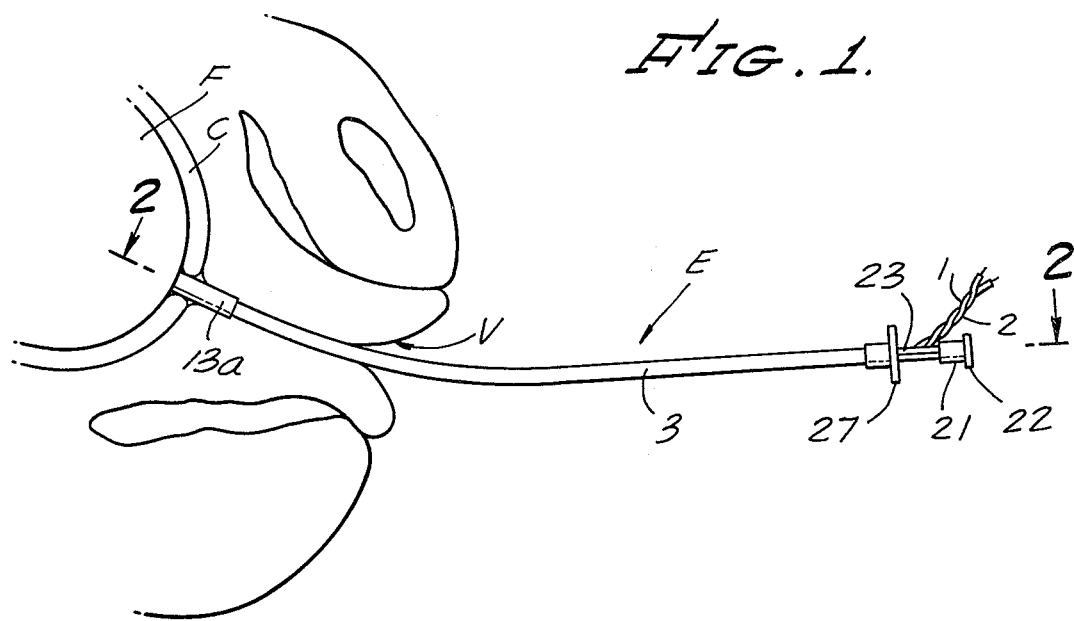
FIG. 1 is a diagrammatic view illustrating one embodiment of an improved electrode structure and applicator constructed in accordance with the teachings of the present invention, with the forward end of the structure inserted through the vagina and cervix of a mother in labor, prior to actuation of the plunger assembly and removal of the inserter tube and plunger assembly.

Referring to FIG. 1, the forward end of electrode structure E of the embodiment of the present invention shown in FIGS. 1-9 is adapted to be inserted through the vagina V and the cervix C of a mother in labor. The electrode structure E includes an elongated inserter tube 3 which is generally form-sustaining and which is curved to generally conform to and fit the angular anatomical configuration of a woman's vagina and cervix so as to be adapted to be comfortably inserted therethrough. The inserter tube 3 is open at its forward and rear ends.

Figure 5:
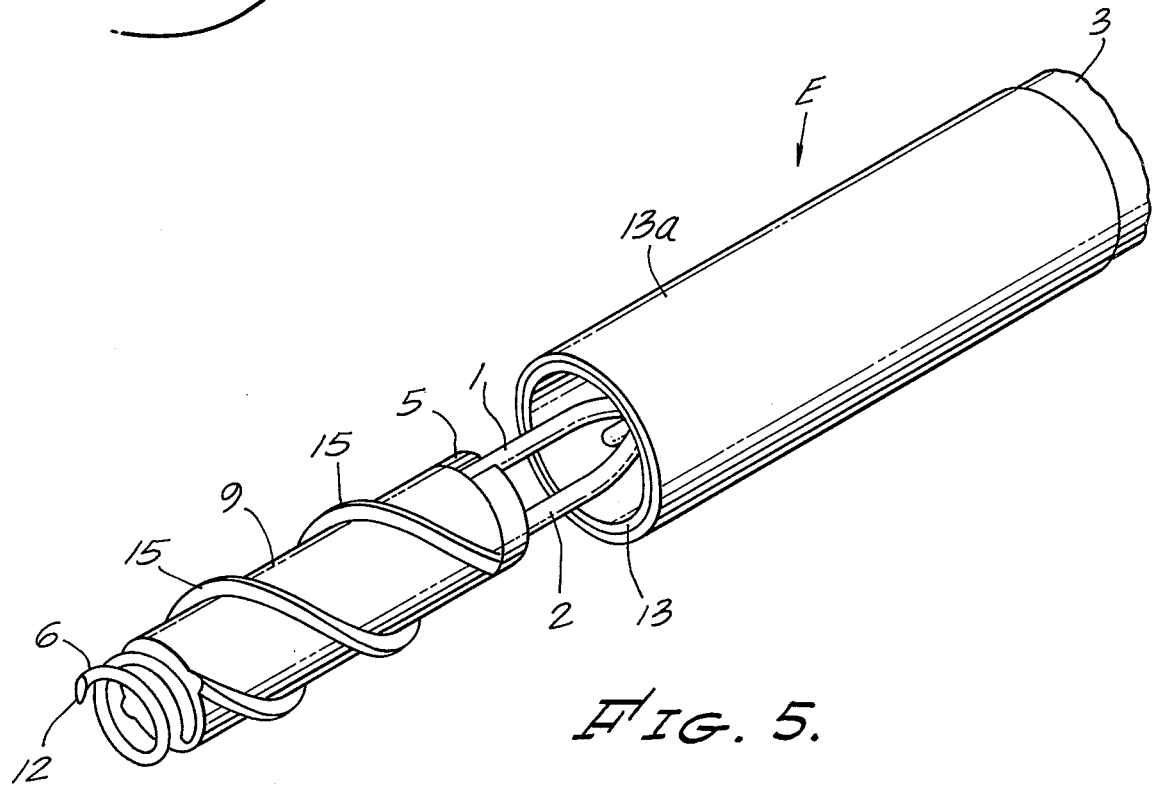
FIG. 5 is a perspective view showing the forward end of the improved electrode applicator structure (shown in FIGS. 1-4) with the electrode carrying member projecting forwardly of the forward end of the inserter tube.

As best shown in FIGS. 2A and 5 the electrode applicator structure E further comprises first and second electrodes 5 and 6 connected, respectively, to the rear and forward ends of a generally cylindrical electrode carrying member 9. The electrodes 5 and 6 are preferably made of stainless steel and have electrical wires 1 and 2 suitably connected (e.g., soldered) thereto. The electrode-carrying member 9 is made of an electrically insulative material, such as plastic. The wires 1 and 2 extend through the inserter tube 3 and are adapted to have their outer ends connected to a suitable monitoring apparatus (not shown). Electrode 5 is generally of cylindrical or disc shape and has an opening 7 in its peripheral edge through which the wire 1 extends (see FIGS. 2A and 6A). The wire 1 is insulated throughout most of its length but has a bared forward end 8 connected (e.g., soldered) to the electrode 5. Wire 2, also insulated, extends through the electrodecarrying member 9 and has a bared end 10 soldered to the end 11 of electrode 6. Wire 2 extends from electrode 6 through the electrode-carrying member 9 and thence through an opening in the periphery of electrode 5. The electrode 6 is of generally helical or spiral configuration and has its rear end embedded in the forward end of member 9. The forward end of coiled electrode 6 terminates in a pointed end 12 which is adapted to penetrate the epidermis of the fetus F (FIGS. 1, 8 and 9) in the mother's uterus.

All of the soldered connections are epoxy coated to insulate them.

A plastic sleeve 13 is mounted on the forward end of the the guide tube 3 by an outer support sleeve or ferrule 13a which extends beyond the rear end of the sleeve 13 and extends over the forward end 13b of the tube 3. The support sleeve 13a is preferably made of stainless steel.

Double lead helical grooves 14 are formed in the interior wall of the plastic sleeve 13, and companion double lead helical ribs 15 are provided on the outer surface of the electrode-carrying member 9. Preferably the helix angle of the ribs and grooves is such that forward longitudinal movement of the electrode-carrying member 9 from the fully retracted position (FIG. 2A) will cause the electrode-carrying member 9 and spiral electrode 6 to rotate through a predetermined arc, e.g., 360 degrees or one revolution. Thus, the pointed, helical electrode 6 can only be inserted into the epidermis of the fetus to a predetermined extent. Such penetration will be determined by the extent of rotation of the electrode-carrying member 9, as it is projected from the sleeve 13, and the helix angle of the spiral electrode 6.

When the electrode-carrying member 9 is in the fully retracted position shown in FIG. 2A, the pointed tip 12 of the spiral electrode 6 is retracted to a location fully housed within the plastic sleeve 13 on the forward end of the inserter tube 3. Thus, the pointed tip 12 can do no damage to the vaginal or cervical tissue of the mother during insertion.

The electrode structure E is equipped with a plunger assembly P for projecting the electrode-carrying member 9 forwardly (and consequently causing it to simultaneously rotate). The plunger assembly P includes an elongated, laterally flexible, axially rigid plunger rod 16 which extends longitudinally through a substantial portion of the length of the inserter tube 3. The inner or forward end 17 of the plunger rod is preferably rounded and engages a conical seat 18 on the rear surface of the cylindrical electrode 5 (FIGS. 2B and 6B). This structure permits free rotation of the electrode-carrying member 9 as it is projected forwardly.

The plunger rod 16 extends through a tubular passage 19 provided on the interior wall of the inserter tube 3, e.g., by a tubular member 19a secured along the interior wall of the inserter tube.

As seen in FIGS. 2B and 6B, the rear end of the plunger rod 16 is embedded in a plunger head 21 having an enlarged thumb piece 22 thereon and an elongated plunger shaft 23 which extends into the inserter tube 3. The underside of the plunger shaft 23 (as viewed in FIGS. 2B and 4) has an elongated arcuate groove 24 therein which slidably receives the tubular member 19a forming passage 19 as the plunger shaft 23 and rod 16 are moved longitudinally within the inserter tube. This structure prevents relative rotation between the plunger P and the inserter tube 3.

The plunger shaft 23 and the inserter tube 3 are provided with cooperative wire holding elements to hold the wires 1 and 2 in a fixed position prior to the time it is desired to project the spiral electrode 6 into the fetus. As shown in FIGS. 2B, 4 and 6B, these holding elements comprise a radially outwardly projecting lug 25 on the plunger shaft 23 and a radially inwardly projecting lug 26 on the interior wall of the inserter tube 3 near the rear end thereof. When the lugs 25 and 26 are in the confronting relationship illustrated in FIGS. 2B and 4, the electrode wires 1 and 2 are frictionally clamped therebetween. When the plunger structure P is pressed inwardly into the inserter tube 3, as shown in FIG. 6B, the clamping action is relieved since lugs 25 and 26 are no longer in a confronting relationship, and the wires 1 and 2 may move forwardly with the electrode-carrying member 9.

Depression of the plunger structure P is facilitated by provision of a finger engaging flange 27 (see FIGS. 2B, 8 and 9) on the rear end of the inserter tube 3.

In use, inserter tube 3 is inserted through the vagina V and cervix C of the patient and into contact with the fetus F, as shown in FIG. 1. Thereafter, the plunger P is depressed (FIG. 8), releasing the frictional clamp on the wires 1 and 2 and progressively causing forward movement of the electrode-carrying member body 9. As the electrode-carrying member 9 moves forwardly, the cooperating helical grooves 14 and 15 cause rotation of the helical electrode 6 through a predetermined arc to penetrate and engage the fetal epidermis. Thereafter, the inserter tube 3 is removed from the mother, leaving the electrode structure in place, as illustrated in FIG. 9.

The primary difference between the embodiment shown in FIG. 10, compared to the embodiment of FIGS. 1-9, is that in the FIG. 10 embodiment the helical grooves 114 are formed in the outer peripheral surface of the electrode carrying member 109 and the companion ribs 115 are provided on the interior wall of the sleeve 113 on the forward end of the inserter tube 103. The forward end of the plunger rod 116 engages the conical seal 118 of the electrode member 105. The wire 101 has its bared end 108 electrically connected, as by soldering, to the electrode 105. The wire 102 extends longitudinally through the electrode-carrying member 109 and has its bared end 110 connected, as by soldering, to the coiled electrode 106.

The FIG. 10 embodiment also includes a stop ring or flange 130 which projects radially inwardly to limit rearward (or inward) movement of the electrode-carrying member 109. Thus, when the electrode-carrying member 109 is retracted and the electrode wires 101 and 102 are clamped, both inward and outward movement of the electrode-carrying member are prevented.

DESCRIPTION OF THE EMBODIMENT OF FIGS. 11-17B

Referring to FIG. 11, the forward end of the electrode structure EE of the embodiment of the present invention shown in FIGS. 11-17B is adapted to be inserted through the vagina and cervix of a mother in labor. The electrode structure EE includes an elongated inserter tube 103 which is generally form-sustaining and which is curved to generally conform to and fit the angular anatomical configuration of a woman's vagina and cervix so as to be adapted to be comfortably inserted therethrough. The inserter tube 103 is open at its forward and rear ends.

Referring to FIGS. 12A and 17A, the electrode applicator structure EE further comprises a generally helical or coil electrode 106 having its rear end portion embedded in an electrode-carrying member 109 and projecting forwardly (i.e., to the left, as viewed in FIGS. 12A and 17A) therefrom. The forwardly-projecting end 112 of electrode 106 is pointed to facilitate penetration of the skin of a fetus when the forward end of the applicator structure EE is inserted through the mother's vagina and actuated as described hereinafter.

The electrode-carrying member 109 also carries a second electrode 105, preferrably of an annular configuration, attached to its rear end.

The electrodes 105 and 106 are preferably made of stainless steel and have electrical wires 101 and 102 suitably connected (e.g., soldered) thereto.

The electrode-carrying member 109 is preferably made of an electrically insulative material such as plastic. The electrode carrying member 109 is disposed in a cup-shaped portion 152 of a motion converter-transmitter 150. The cross-sectional shapes of the electrode-carrying member 109 and the interior wall of the cup-shaped portion 152 may be non-circular (e.g., octagonal, is shown in FIG. 13, so that rotational force and motion of the motion converter 150 will be transmitted to the electrode-carrying member 109 and the coil electrode 106.

The outer diameter of the electrode-carrying member 109 is preferably somewhat smaller than the inside diameter of the cup-shaped portion 152 so that the electrode-carrying member 109 sits somewhat loosely in the cup-shaped member. By virtue of this structure, while rotational motion of the cup-shaped member 152 transmits rotational movement to the electrode-carrying member 109 and the coil electrode 106, excessive torque applied to the cup-shaped member 152 will cause it to "slip" around the electrode-carrying member, thereby preventing potential harm to the fetus.

The wires 101 and 102 extend through the inserter tube 103 and are adapted to have their outer ends 105', 106' connected to a suitable monitoring apparatus (not shown).

Electrode 105 is generally of cylindrical or disk shape and has a central opening 107 through which the wires 101 and 102 extend (see FIG. 12A).

The wire 101 is insulated throughout most of its length but has bared forward end 108 connected (e.g., soldered) to the electrode 105. Wire 102 is also insulated throughout most of its length, extends through the rear portion of the electrode-carrying member 109 and has a bared end 110 soldered to the rear end 111 of coil electrode 106.

All of the soldered connections are preferably epoxy coated to insulate them.

A plastic sleeve 113' is mounted on the forward end of the inserter tube 103, as by a peripheral crimp 115' (FIGS. 12A and 17A), for example. The forward end of the sleeve 113' has a radially inwardly extending, peripheral flange 117 integrally connected thereto for limiting forward movement of the cup-shaped member 152 in a manner described hereinafter.

The electrode applicator structure EE is equipped with a plunger assembly PP (FIGS. 12B and 17B) for projecting the electrode-carrying member 109 and coil electrode 106 forwardly and rotating them. The plunger assembly PP includes an elongated, laterally flexible, axially rigid plunger tube 116 which extends longitudinally through a substantial portion of the inserter tube 103.

The forward end of the plunger tube 116 has a pair of radially inwardly extending projections 118, 118 integrally formed on its interior peripheral wall for engaging helical grooves 158, 158 on a linear-to-rotary converter member 150, as described more fully hereinafter.

Since the inserter tube 103 and the plunger tube 116 are curved, with substantially the same degree of curvature, relative rotational movement therebetween is inhibited.

The rear end of the plunger tube 116 includes a longitudinally extending guide slot 120 which cooperates with a radially inwardly projecting ridge 122 on the rear end of the inserter tube 103 to limit rearward movement of the plunger tube in the inserter tube and to further inhibit relative rotational movement between the inserter tube and the plunger tube. See FIGS. 12B and 15.

As best shown in FIGS. 12B and 17B the rear end of the plunger tube 116 is embedded in a plunger head 121.

Depression of the plunger tube 116 is facilitated by provision of a finger engaging flange 127 on a bushing 128 attached to the rear end of the inserter tube 103, as best shown in FIGS. 12B and 17B.

The electrode applicator structure EE of the present invention includes a linear-to-rotary motion converter 150 disposed between the plunger tube 116 and the electrode carrying member 109 for translating linear force applied to the plunger head 121 to first linear and then rotary motion of the electrode carrying member 109 and the coil electrode 106.

The motion converter 150 includes a generally cup-shaped portion 152 on its forward end and a rearwardly extending tubular shaft 154.

The cup-shaped portion 152 carries the electrode-carrying member 109, and its interior peripheral wall 156 is octagonally shaped (see FIG. 13) to conform to the octagonal cross-sectional shape of the electrode-carrying member 109, whereby rotary motion of the converter 150 and cup-shaped portion 152 will result in rotary motion of the electrode carrying member 109 and the coil electrode 106.

The conversion of linear to rotary motion is accomplished by means of double lead helical grooves 158 in the exterior wall of the rearwardly extending shaft 154 and the radially inwardly extending pins 118, 118 in the forward end of the plunger tube 116. Linear movement of the plunger tube 116 in a forward direction (i.e., to the left as viewed in the drawings) from the position of FIG. 12A to the position of FIG. 17A will, by virtue of the pins 118 engaging the helical grooves 158, cause the motion converter 150, the electrode carrying member 109 and the coil electrode 106 to rotate, since the plunger tube 116 is constrained against rotary movement relative to the inserter tube 103.

The electrode applicator EE includes structure for limiting forward movement of the coil electrode 106 in order to provide a uniformly stable structure during rotation which also insures against unnecessary harm to the fetus since forward movement of the coil electrode is completely controlled.

As best shown in FIGS. 12A and 17A, a radially inwardly extending peripheral flange 117 is provided on the forward end of the plastic sleeve 113 on the forward end of the inserter tube 103. The interior peripheral edge 162 of the flange 117 is large enough to permit movement of the forward end of the electrode carrying member 109 there through, but small enough to engage and stop the forward end of the cup-shaped portion 152 of the motion convertor 150 (see FIG. 17A). Thus, once the motion converter has been projected forwardly to the point shown in FIG. 17A, the coil electrode 106 cannot advance further forwardly, and continued depression on the plunger tube 116 will result only in rotary motion of the motion converter 150 and the electrode-carrying member 109 and coil electrode 106 carried thereby.

As shown in FIGS. 12A and 17A, the rear portion of the cup-shaped portion 152 of the motion converter 150 is flared radially outwardly at its rear end to provide a peripheral edge 164 which engages the forward end 166 of the inserter tube 103 to limit rearward movement of the motion converter 150.

A peripheral crimp 168 is provided around the sleeve 113', forwardly of the crimp 115' and the forward end 166 of the inserter tube 103, to positively hold the motion converter 150 in the position shown in FIG. 12A prior to use of the applicator. When the attending physician introduces the inserter tube 103 into the mother's vagina and positions the applicator structure preparatory to applying the coil electrode 106 to the fetal epidermis, depression of the plunger tube 116 will cause the flared rear peripheral edge 164 of the cup-shaped portion 152 of the motion converter 150 to override the peripheral crimp 168 and permit the coil electrode to be moved forwardly to the position shown in FIG. 17A.

The distance between the forward end 166 of the inserter tube 103 and the peripheral stop flange 117 on the sleeve 113' may be selected to insure that the electrode-carrying member 109 and the coil electrode 106 will move forwardly only a predetermined distance necessary to penetrate the fetal epidermis.

As shown in phantom lines in FIGS. 12B and 16, the applicator structure EE of the FIGS. 11-17 embodiment may be equipped with a locking mechanism to hold the plunger tube 116 rod in retracted the position shown in FIGS. 11, 12A and 12B during shipping and storage, prior to use. The locking mechanism includes a generally flexible tubular piece 180 formed with an opening 182 into which the outer ends 105' and 106' of wires 105 and 106 may be inserted and retained.

When it is desired to use the applicator structure EE, the outer ends of wires 105 and 106 are removed from the opening 182 and the tubular piece 180 is slipped off of the outer end of the plunger tube 116.

The forward end of the inserter tube 103 may then be inserted through the vagina and cervix of the mother and into contact with the fetus. Thereafter, the plunger head 121 is depressed to drive the plunger tube 116, motion converter 150, electrode carrying member 109 and coil electrode 106 forwardly, to the position shown in FIG. 17A, wherein the pointed forward end 112 of the coil electrode 106 engages and penetrates the skin of the fetus. When the motion converter 150 is pressed forwardly, the flared rear peripheral edge 164 of the cup-shaped portion 152 overrides the inwardly-projecting radial crimp 168 in the sleeve 113'. Forward movement of the coil electrode 106 is limited by the forward end 151 of the cup-shaped portion 152 engaging the peripheral flange 117 of the sleeve 113', as shown in FIG. 17A.

As the plunger head 121 is further depressed, the resulting linear force 121 will, by virtue of the pins 118 engaging the double helical groove 158 in the outer surface of the shaft portion 154 of motion converter 150, cause the motion converter 150 and the electrode carrying member 109 carried thereby to rotate, thereby rotating the coil electrode 106 into the fetal epidermis FF (FIG. 17A).

While the particular embodiment of the electrode structure EE depicted in FIGS. 11-17 utilizes non-circular (e.g., octagonal) cross-sectional shapes of the electrode carrying member 109 and the interior peripheral wall of the cup-shaped member 152 of the motion converter 150 to the electrode carrying member 109 and the coil electrode 106, it is contemplated that any other suitable structure may be employed for this purpose. For example, it is contemplated that the slot structure of the invention of U.S. Pat. No. Re. 28,990 may be employed. See, e.g., FIG. 8 of the U.S. Pat. No. Re. 28,990 wherein the second electrode 222 is engaged by slots 252, 252 on the forward end of a tubular drive member 254, whereby rotational movement and force of the drive tube 254 is transmitted to the electrode carrying member 214 via the flat electrode 222. This drive structure may be incorporated in the embodiment EE of FIGS. 11-17B by making the electrode 105 flat (similar to the electrode 222 of FIG. 8 of U.S. Pat. No. Re. 28,990) and forming slots in the motion converter 150.

ADVANTAGES

From the foregoing it is believed that the advantages of the present invention over U.S. Pat. No. Re. 28,990 may be appreciated. The electrode applicator structure of the present invention is safer in that the degree of rotation of the spinal electrode is completely controlled, i.e., the physician cannot turn the electrode-carrying member and the spiral electrode through more than a predetermined arc (e.g., one revolution), thus greatly reducing the possibility of fetal damage from excessive electrode rotation. Another advantage of the structure of the present invention is that the electrode-carrying member and the electrode mounted therein are positively held in position within one forward end of the inserter tube by virtue of the cooperating ribs and grooves. Consequently, the possibility of electrode rotation failure (due to inadvertent disassembly of the electrode rotating mechanism during insertion through the vagina and cervical canal) is greatly reduced.

Further, the spiral electrode is held in a completely retracted position within the inserter tube, thereby avoiding damage to the tissue of the mother during insertion of the structure.

Still further, actuation of the device to engage the spiral electrode in the fetal epidermis is affected automatically by simply depressing the plunger structure. It is unnecessary to disengage any wedge or lock mechanism by a separate motion.

The embodiment shown in FIGS. 11-17B offer additional advantages not realized by the embodiments of FIGS. 1-10, for example:

(1) In the FIGS. 11-17B structure, the distance of projection of the coil electrode 106 beyond the end of the inserter tube 103 can be controlled. In the embodiments of FIGS. 1-10, the extent of projection is related to the position of the helixes, and rotational stability of the coil electrode decreases as the electrode rotates.

With the improved structure of the embodiment of FIGS. 11–17B, the extent of linear movement of the electrode is limited and adjustable to provide uniform stability during rotation.

(2) The amount of rotation (i.e., the number of turns) of the coil electrode may be readily controlled by selecting predetermined lengths of the helical tracks in the electrode carrying member 109. In the embodiment of FIGS. 1–10, rotational control requires changing the length and/or diameter of the electrode carrying member 9.

(3) The structure of the FIGS. 11–17B embodiment is simpler and somewhat more desirable in that the need for having the plunger rod (of the FIGS. 1–10 embodiments) seat in the conical depression in the rear end of the second electrode 5 has been eliminated and the functions of the plunger and part of the rotating mechanism have been combined into a single unit.

(4) The annular shape of the electrode 105 permits the electrode wires to pass conveniently through its center, thereby providing for excellent electrical and mechanical stability.

(5) The design of the applicator structure EE provides a simple and convenient method for attaching various types of sensors to the fetus, with or without the use of resins, adhesives or glues.

(6) The locking mechanism limits the range of movement of the plunger.

It is contemplated that various modifications, additions and deletions of structure may be made to the particular illustrative embodiments described above shown in the drawings without departing from the spirit and scope of this invention. (By way of example only, it is contemplated that hydraulic or pneumatic means or a spring mechanism may be employed to effect application of the electrode structure). Accordingly, it is intended that the present invention be limited only by the scope of the appended claims.

I claim:

1. An apparatus for use in monitoring fetal heartbeat and the like comprising:
    a tubular member having a forward end and a rearward end, the forward end adapted to be inserted through the vagina and cervix of a woman in labor;
    an electrode structure having a forward portion and a rearward portion movably mounted in said tubular member;
    said electrode structure comprising an electrode carrying member and a coil electrode at its forward portion adapted to be attached to the skin of a fetus upon projection thereof through the forward end of the tubular member and rotation of said coil electrode; and
    means associated with said electrode structure for converting linear motion to rotary motion for rotating and projecting said electrode structure through the forward end of said tubular member responsive to linear motion.

2. The apparatus of claim 1, wherein said means associated with said electrode structure for converting linear to rotary motion for rotating and projecting said electrode structure includes cooperating ribs and grooves on said electrode carrying member and said tubular member for causing rotation of said electrode carrying member and said coil electrode attached thereto when said electrode carrying member is moved forwardly in said tubular member responsive to a linear movement, said ribs and grooves having a generally helical configuration.

3. The apparatus of claim 2, wherein said grooves are formed on the interior peripheral wall of the forward end of said tubular member, and wherein said ribs are formed on the exterior surface of said electrode carrying member.

4. The apparatus of claim 2, wherein said grooves are formed in the exterior surface of said electrode carrying member and said ribs are provided on the interior peripheral wall of said tubular member.

5. The apparatus of claim 2, wherein said electrode structure further includes a plunger assembly and the movement of said electrode carrying member is responsive to the linear movement of said plunger assembly.

6. The apparatus of claim 5, wherein said plunger assembly includes a plunger head at the rearward end of said tubular member and a plunger rod extending between said plunger head and said electrode carrying member.

7. The apparatus of claim 5, wherein said electrode structure further includes a second electrode spaced from said coil electrode; and further including an electrical wire attached to each of said coil electrode and said second electrode and extending rearwardly through said tubular member; and further including cooperable clamping means on said tubular member and said plunger assembly for maintaining said wires in a relatively fixed position.

8. The apparatus of claim 1, wherein said electrode structure further includes a second electrode spaced from said coil electrode; and further including an electrical wire attached to each of said coil electrode and said second electrode and said wires extending rearwardly through said tubular member; and further including means for selectively clamping said wires to prevent relative movement of said wires in said tubular member.

9. An apparatus, comprising:
    a substantially form-sustaining, hollow elongated inserter tube structure having a forward end and a rear end and being curved to conform to and fit the angular anatomical configuration of a woman's vagina and cervix so as to be comfortably inserted through the vagina and cervix;
    an electrode structure, said electrode structure comprising an electrode carrying member and a spiral electrode movably disposed in the forward end of said inserter tube structure, said spiral electrode positioned at the forward end of said tube structure;
    plunger means disposed at the rear end of said inserter tube structure;
    means for rotating and moving said electrode structure out of the forward end of the tube structure in response to linear movement of said plunger means to engage the epidermis of a fetus with said spiral electrode.

10. The apparatus of claim 9 wherein said means for rotating and moving said electrode structure out of the forward end of the tube structure in response to linear movement of said plunger means comprises companion helical ribs and grooves engaged between said electrode structure and said inserter tube structure.

11. The apparatus of claim 9 wherein said means for rotating and moving said electrode structure out of the forward end of the tube structure in response to linear movement of said plunger means comprises a helical rib on said electrode structure and a helical groove in said inserter tube structure receiving said rib.

12. The apparatus of claim 9 wherein said means for rotating and moving said electrode structure out of the forward end of the tube structure in response to linear movement of said plunger means comprises a helical rib in said inserter tube structure and a helical groove on said electrode structure receiving said rib.

13. The apparatus of claim 9 wherein said means for rotating and moving said electrode structure out of the forward end of the tube structure in response to linear movement of said plunger means effects a predetermined angular movement of said spiral electrode during linear movement of said electrode structure.

14. The apparatus of claim 9 wherein said electrode structure further includes a second electrode spaced from said spiral electrode; and further including an electrical wire attached to each of said coil electrode and said second electrode, said wires extending rearwardly through said inserter tube structure; said plunger means comprising clamping means engageable with said wires to clamp said wires in place with said electrode structure retracted in said forward end of said inserter tube structure.

15. The apparatus of claim 9 wherein said plunger means comprises a flexible rod within said hollow inserter tube structure, said flexible rod having one end extending from the rear end of said inserter tube structure and having an inner end in engagement with said electrode structure.

16. The apparatus of claim 15 wherein said rod and said electrode structure having means permitting unrestricted movement of said inner end of said rod.

17. The apparatus of claim 9 wherein said electrode structure includes electrode wires connected to said spiral electrode and to a second electrode associated with said electrode structure spaced from said spiral electrode, and wherein said inserter tube structure has means engageable by said electrode structure to limit inward movement of said electrode structure into the forward end of said inserter tube structure and said plunger means has means releasably engageable with said electrode wires to hold said electrode structure against movement from the forward end of said inserter tube structure.

18. The apparatus of claim 9 wherein said electrode structure includes electrode wires connected to said spiral electrode and to a second electrode associated with said electrode structure spaced from said spiral electrode, and wherein said inserter tube structure has means engageable by said electrode structure to limit inward movement of said electrode structure into the forward end of said inserter tube structure, said plunger means having means releasably engageable with said electrode wires to hold said electrode structure against movement from the forward end of said inserter tube structure, and releasable from said electrode wires upon initial movement of said plunger means into the rear end of said inserter tube structure.

19. The apparatus of claim 9 wherein said plunger means comprises a flexible rod having an inner end extending from said plunger means for releasable driving contact with said electrode structure, said electrode structure having a seat engageable by the inner end of said rod.

20. The apparatus of claim 9 wherein said plunger means comprises a flexible rod extending from said plunger means for releasable driving contact with said electrode structure, said electrode structure having a seat freely engageable by an inner end of said rod, and including guide means extending along one side of said inserter tube structure and slidably receiving said rod, said guide means terminating in spaced relation to the forward end of said inserter tube structure to permit extension of said rod into engagement with said seat from said guide means.

21. The apparatus of claim 9 wherein said plunger means comprises a flexible rod extending from said plunger means for releasable driving contact with said electrode structure, said electrode structure having a seat freely engageable by an inner end of said rod, and including guide means extending along one side of said inserter tube structure for slidably receiving said rod, said guide means terminating in spaced relation to the forward end of said inserter tube structure to permit extension of said rod into engagement with said seat, said plunger means having means slidably engaging said tube structure to prevent rotation of said plunger means relative said inserter tube structure.

22. The apparatus of claim 9 wherein said plunger means comprises a flexible rod extending from said plunger means for releasable driving contact with said electrode structure, said electrode structure having a seat freely engageable by the forward end of said rod, and including guide means extending along one side of said inserter tube structure and slidably receiving said rod, said guide means terminating in spaced relation to the forward end of said inserter tube to permit extension of said rod into engagement with said seat from said guide means, said plunger having means slidably engaging said tube structure to prevent rotation of said plunger means in said inserter tube, and electrode wire clamping means on said plunger means and said inserter tube including clamping members positioned for engagement with electrode wires connected to said coil electrode and to a second electrode associated with said electrode structure spaced from said coil electrode upon retraction of said plunger means and said wires with respect to said inserter tubes to a location at which said electrode means is fully confined within said forward end of said inserter tube.

23. The apparatus of claim 9 wherein said plunger means comprises a flexible rod extending from said plunger means for releasable driving contact with said electrode structure, said electrode structure having a seat freely engageable by the forward end of said rod, and including guide means extending along one side of said inserter tube structure and slidably receiving said rod, said guide means terminating in spaced relation to the forward end of said inserter tube to permit extension of said rod into engagement with said seat from said guide means, said plunger having means slidably engaging said tube structure to prevent rotation of said plunger means in said inserter tube, and electrode wire clamping means on said plunger means and said inserter tube including clamping members positioned for engagement with two electrode wires connected to said electrode structure upon retraction of said plunger means and said electrode wire means with respect to said inserter tube to a location at which said electrode means is fully confined within said forward end of said inserter tube, said inserter tube and said electrode structure having means limiting inward movement of said electrode structure into said inserter tube to said location.

24. An improved applicator structure for attaching a coil electrode to the skin of a fetus, comprising:
  a generally elongated inserter tube having a forward portion adapted to be inserted through the vagina and cervix of a woman in labor and a rear portion;
  an electrode-carrying member disposed in said forward portion of said inserter tube; said electrode-carrying member having a forward end;
  a coil electrode connected to said electrode-carrying member and extending forwardly from the forward end thereof;
  plunger means in said rear portion of said inserter tube; and
  converter means disposed between said plunger means and said electrode-carrying member for converting linear force applied to said plunger means to rotary force applied to said electrode carrying member and said coil electrode.

25. An improved applicator structure according to claim 24, wherein said converter means comprises a helical groove on one of said electrode-carrying member or said inserter tube and a cooperating helical rib on said other of said electrode-carrying member or said inserter tube.

26. An improved applicator structure according to claim 25, wherein said helical groove is formed in said electrode carrying member and said helical rib is formed on said inserter tube.

27. An improved applicator structure according to claim 24, wherein said converter means comprises a motion converter member disposed in said inserter tube; and wherein said plunger means includes a plunger tube having a forward portion disposed in said inserter tube.

28. An improved applicator structure according to claim 27, wherein a helical groove is formed in said motion converter member; and wherein said plunger tube has an interior peripheral wall; and a projection extending from said interior peripheral wall of said plunger tube and engaging said helical groove in said motion converter member.

29. An improved applicator structure according to claim 27, wherein said motion converter member includes a generally cup-shaped forward portion and a tubular shaft extending rearwardly therefrom; said electrode-carrying member being disposed in said cup-shaped portion.

30. An improved applicator structure according to claim 29, wherein said cup-shaped portion includes an interior peripheral wall which is non-circular in cross-section; and wherein said cross-sectional shape of said electrode-carrying member is non-circular, whereby rotational movement of said motion converter member will rotate said electrode-carrying member and the coil electrode attached thereto.

31. An improved applicator structure according to claim 30, wherein the diameter of said electrode-carrying member is sufficiently smaller than the diameter of said interior peripheral wall of said cup-shaped portion, whereby rotational force above a predetermined force applied to said cup-shaped portion will cause said portion to slip around said electrode-carrying member and such force will not be imparted to said electrode-carrying member or said coil electrode.

32. An improved applicator structure for attaching a coil electrode to the skin of a fetus comprising:
  a generally elongated inserter tube having a forward end portion terminating at a forward end, said forward end portion being adaptable to be inserted through the vagina and cervix of a woman in labor, and an open rear end;
  an electrode-carrying member disposed in said forward end portion of said inserter tube; said electrode-carrying member having a forward end;
  a coil electrode connected to said electrode-carrying member and extending forwardly from the forward end thereof;
  a plunger member extending through said open rear end of said inserter tube; and
  a force transfer means comprising a force transfer member disposed in said inserter tube between said plunger member and said electrode-carrying member for transferring and converting substantially linear force applied to said plunger member to said electrode-carrying member to move said coil electrode through the forward end of said inserter tube and rotate said electrode carrying member.

33. An improved applicator structure according to claim 32 and further including means limiting forward movement of said electrode-carrying member so as to limit the distance which said coil electrode can move beyond the forward end of said inserter tube.

34. An improved applicator structure according to claim 33 wherein said means limiting forward movement of said electrode-carrying member comprises abutment means on said force transfer member and on said forward end of said inserter tube.

35. An improved applicator structure according to claim 32 wherein said force transfer member includes a generally elongated member having a rear portion in the form of a generally tubular shaft, and a generally cup-shaped forward portion; said electrode-carrying member being disposed in said cup-shaped forward portion.

36. An improved applicator structure according to claim 35 wherein said cup-shaped portion includes an inner peripheral wall, and wherein said inner peripheral wall of said cup-shaped forward portion of said force transfer member and the outer peripheral wall of said electrode carrying member are of substantially the same cross-sectional shape, and are non-circular in shape, whereby rotary motion of said force transfer member will transfer rotational movement to said electrode carrying member and said coil electrode.

37. An improved applicator structure according to claim 36 wherein the inner diameter of said cup-shaped portion is somewhat larger than the outer diameter of said electrode carrying member, whereby said cup-shaped portion can slip around said electrode-carrying member when rotational force above a predetermined level is applied to said force transfer member when said coil electrode is engaged in a fetus.

38. An improved applicator structure according to claim 35 wherein the outer wall of said generally tubular shaft of said force transfer member has a helical groove therein; and wherein said plunger member is a tubular member having an inner wall having a radially inwardly projecting portion extending into said helical groove; and further including means preventing relative rotational movement between said inserter tube and said plunger member; whereby substantially linear force applied to said plunger member causes rotational movement of said force transfer member.

39. An improved applicator structure according to claim 35 wherein said forward end of said inserter tube has a radially inwardly extending flange portion thereon; said flange portion and said forward end portion of said cup-shaped portion of said force transfer member comprises abutment means for limiting forward movement of said electrode coil.

40. An improved applicator structure according to claim 35 and further comprising cooperating abutment means on the rear end of said cup-shaped portion of said force transfer member and on said inserter tube for limiting rearward movement of said force transfer member in said inserter tube.

41. An improved applicator structure according to claim 32 and further comprising means for normally holding said force transfer member in a predetermined position in said inserter tube; said means including means adapted to be overridden upon the application of forward force upon said force transfer member above a predetermined force.

42. An improved applicator structure according to claim 33 wherein said means limiting forward movement of said electrode carrying member includes a radially outwardly flared portion on said force transfer means and a radially inwardly projecting portion on said inserter tube.

43. An apparatus for use in monitoring fetal heartbeat and the like comprising:
- a tubular member having a forward end and a rearward end, the forward end adapted to be inserted through the vagina and cervix of a woman in labor;
- an electrode structure having a forward portion and a rearward portion movably mounted in said tubular member;
- said electrode structure comprising an electrode carrying member and a coil electrode at its forward portion adapted to be attached to the skin of a fetus upon projection thereof through the forward end of the tubular member and rotation of said coil electrode; and
- means for substantially simultaneously moving said electrode structure through the forward end of said tubular member and rotating same, said means for moving and rotating said electrode structure includes cooperating ribs and grooves on said electrode carrying member and said tubular member for causing rotation of said electrode carrying member and said coil electrode attached thereto when said electrode carrying member is moved forwardly in said tubular member, said ribs and grooves having a generally helical configuration, wherein said grooves are formed on the interior peripheral wall of the forward end of said tubular member, and wherein said ribs are formed on the exterior surface of said electrode carrying member.

44. An apparatus for use in monitoring fetal heartbeat and the like comprising:
- a tubular member having a forward end and a rearward end, the forward end adapted to be inserted through the vagina and cervix of a woman in labor;
- an electrode structure having a forward portion and a rearward portion movably mounted in said tubular member;
- said electrode structure comprising an electrode carrying member and a coil electrode at its forward portion adapted to be attached to the skin of a fetus upon projection thereof through the forward end of the tubular member and rotation of said coil electrode;
- means for substantially simultaneously moving said electrode structure through the forward end of said tubular member and rotating same, said means for moving and rotating said electrode structure includes cooperating ribs and grooves on said electrode carrying member and said tubular member for causing rotation of said electrode carrying member and said coil electrode attached thereto when said electrode carrying member is moved forwardly in said tubular member, said ribs and grooves having a generally helical configuration; and
- a plunger assembly, the movement of said electrode carrying member responsive to the linear movement of said plunger assembly;
- said plunger assembly includes a plunger head at the rearward end of said tubular member and a plunger rod extending between said plunger head and said electrode carrying member.

45. An electrode structure apparatus, comprising:
- a substantially form-sustaining, elongated inserter tube structure having a forward end and a rear end and being curved to conform to and fit the angular anatomical configuration of a woman's vagina and cervix so as to be comfortably inserted through the vagina and cervix;
- an electrode structure, said electrode structure comprising an electrode carrying member and a spiral electrode movably disposed in the forward end of said inserter tube structure, said spiral electrode positioned at the forward end of said tube structure and wherein said electrode structure includes electrode wires connected to said spiral electrode and to a second electrode associated with said electrode structure spaced from said spiral electrode;
- plunger means reciprocably disposed at the rear end of said inserter tube structure;
- means for rotating and moving said electrode structure out of the forward end of the tube structure in response to axial projection of said plunger means to engage the epidermis of a fetus with said spiral electrode; and
- means actuatable by said plunger means upon inward movement into the rear end of said inserter tube structure to axially project said electrode structure and cause rotation thereof;
- said inserter tube structure has means engageable by said electrode structure to limit inward movement of said electrode structure into the forward end of said inserter tube structure and said plunger means has means releasably engageable with said electrode wires to hold said electrode structure against movement from the forward end of said inserter tube structure.

46. An electrode structure apparatus, comprising:
- a substantially form-sustaining, elongated inserter tube structure having a forward end and a rear end and being curved to conform to and fit the angular anatomical configuration of a woman's vagina and cervix so as to be comfortably inserted through the vagina and cervix;
- an electrode structure, said electrode structure comprising an electrode carrying member and a spiral electrode movably disposed in the forward end of said inserter tube structure, said spiral electrode positioned at the forward end of said tube structure and wherein said electrode structure includes electrode wires connected to said spiral electrode and to a second electrode associated with said electrode structure spaced from said spiral electrode;

plunger means reciprocably disposed at the rear end of said inserter tube structure;

means for rotating and moving said electrode structure out of the forward end of the tube structure in response to axial projection of said plunger means to engage the epidermis of a fetus with said spiral electrode; and means actuatable by said plunger means upon inward movement into the rear end of said inserter tube structure to axially project said electrode structure and cause rotation thereof; said inserter tube structure has means engageable by said electrode structure to limit inward movement of said electrode structure into the forward end of said inserter tube structure, said plunger means having means releasably engageable with said electrode wires to hold said electrode structure against movement from the forward end of said inserter tube structure, and releasable from said electrode wires upon initial movement of said plunger means into the rear end of said inserter tube structure.

47. An electrode structure apparatus, comprising:

a substantially form-sustaining, elongated inserter tube structure having a forward end and a rear end and being curved to conform to and fit the angular anatomical configuration of a woman's vagina and cervix so as to be comfortably inserted through the vagina and cervix;

an electrode structure, said electrode structure comprising an electrode carrying member and a spiral electrode movably disposed in the forward end of said inserter tube structure, said spiral electrode positioned at the forward end of said tube structure;

plunger means reciprocably disposed at the rear end of said inserter tube structure;

means for rotating and moving said electrode structure out of the forward end of the tube structure in response to axial projection of said plunger means to engage the epidermis of a fetus with said spiral electrode; and means actuatable by said plunger means upon inward movement into the rear end of said inserter tube structure to axially project said electrode structure and cause rotation thereof;

said means actuatable by said plunger means comprises a flexible rod extending from said plunger means for releasable driving contact with said electrode structure, said electrode structure having a seat freely engageable by an inner end of said rod, and including guide means extending along one side of said inserter tube structure and slidably receiving said rod, said guide means terminating in spaced relation to the forward end of said inserter tube structure to permit extension of said rod into engagement with said seat from said guide means.

48. An electrode structure apparatus, comprising:

a substantially form-sustaining, elongated inserter tube structure having a forward end and a rear end and being curved to conform to and fit the angular anatomical configuration of a woman's vagina and cervix so as to be comfortably inserted through the vagina and cervix;

an electrode structure, said electrode structure comprising an electrode carrying member and a spiral electrode movably disposed in the forward end of said inserter tube structure, said spiral electrode positioned at the forward end of said tube structure;

plunger means reciprocably disposed at the rear end of said inserter tube structure;

means for rotating and moving said electrode structure out of the forward end of the tube structure in response to axial projection of said plunger means to engage the epidermis of a fetus with said spiral electrode; and means actuatable by said plunger means upon inward movement into the rear end of said inserter tube structure to axially project said electrode structure and cause rotation thereof;

said means actuatable by said plunger means comprises a flexible rod extending from said plunger means for releasable driving contact with said electrode structure, said electrode structure having a seat freely engageable by an inner end of said rod, and including guide means extending along one side of said inserter tube structure for slidably receiving said rod, said guide means terminating in spaced relation to the forward end of said inserter tube structure to permit extension of said rod into engagement with said seat, said plunger means having means slidably engaging said tube structure to prevent rotation of said plunger means relative said inserter tube structure.

49. An electrode structure apparatus, comprising:

a substantially form-sustaining, elongated inserter tube structure having a forward end and a rear end and being curved to conform to and fit the angular anatomical configuration of a woman's vagina and cervix so as to be comfortably inserted through the vagina and cervix;

an electrode structure, said electrode structure comprising an electrode carrying member and a spiral electrode movably disposed in the forward end of said inserter tube structure, said spiral electrode positioned at the forward end of said tube structure and wherein said electrode structure includes electrode wires connected to said spiral electrode and to a second electrode associated with said electrode structure spaced from said spiral electrode;

plunger means reciprocably disposed at the rear end of said inserter tube structure;

means for rotating and moving said electrode structure out of the forward end of the tube structure in response to axial projection of said plunger means to engage the epidermis of a fetus with said spiral electrode; and means actuatable by said plunger means upon inward movement into the rear end of said inserter tube structure to axially project said electrode structure and cause rotation thereof;

said means actuatable by said plunger means comprises a flexible rod having a forward end extending from said plunger means for releasable driving contact with said electrode structure, said electrode structure having a seat freely engageable by said forward end of said rod, and including guide means extending along one side of said inserter tube structure and slidably receiving said rod, said guide means terminating in spaced relation to the forward end of said inserter tube structure to permit extension of said rod into engagement with said seat from said guide means, said plunger means having means slidably engaging said tube structure to prevent rotation of said plunger means in said inserter tube structure, and electrode wire clamping means on said plunger means and said inserter tube structure including clamping members positioned for engagement with said electrode wires upon retraction of said plunger means and said wires with respect to said inserter tube structure to a location at which said electrode structure is fully confined within said forward end of said inserter tube structure.

50. An electrode structure apparatus, comprising:
a substantially form-sustaining, elongated inserter tube structure having a forward end and a rear end and being curved to conform to and fit the angular anatomical configuration of a woman's vagina and cervix so as to be comfortably inserted through the vagina and cervix;
an electrode structure, said electrode structure comprising an electrode carrying member and a spiral electrode movably disposed in the forward end of said inserter tube structure, said spiral electrode positioned at the forward end of said tube structure and wherein said electrode structure includes electrode wires connected to said spiral electrode and to a second electrode associated with said electrode structure spaced from said spiral electrode;
plunger means reciprocably disposed at the rear end of said inserter tube structure;
means for rotating and moving said electrode structure out of the forward end of the tube structure in response to axial projection of said plunger means to engage the epidermis of a fetus with said spiral electrode; and
means actuatable by said plunger means upon inward movement into the rear end of said inserter tube structure to axially project said electrode structure and cause rotation thereof;
said means actuatable by said plunger means comprises a flexible rod having a forward end extending from said plunger means for releasable driving contact with said electrode structure, said electrode structure having a seat freely engageable by said forward end of said rod, and including guide means extending along one side of said inserter tube structure and slidably receiving said rod, said guide means terminating in spaced relation to the forward end of said inserter tube structure to permit extension of said rod into engagement with said seat from said guide means, said plunger means having means slidably engaging said inserter tube structure to prevent rotation of said plunger means in said inserter tube structure, and electrode wire clamping means on said plunger means and said inserter tube structure including clamping members positioned for engagement with said electrode wires upon retraction of said plunger means and said electrode wires with respect to said inserter tube structure to a location at which said electrode structure is fully confined within said forward end of said inserter tube structure, said inserter tube structure and said electrode structure having means limiting inward movement of said electrode structure into said inserter tube structure to said location.

* * * * *